United States Patent [19]

Jacobs

[11] Patent Number: 5,610,138
[45] Date of Patent: *Mar. 11, 1997

[54] PROCESS FOR TREATING INFERTILITY AND AN AGENT FOR USE IN THE PROCESS

[75] Inventor: Howard S. Jacobs, London, England

[73] Assignee: Novo Nordisk A/S, Bagsvaerd, Denmark

[*] Notice: The term of this patent shall not extend beyond the expiration date of Pat. No. 5,063,204.

[21] Appl. No.: 430,513

[22] Filed: Apr. 27, 1995

Related U.S. Application Data

[63] Continuation of Ser. No. 299,958, Sep. 1, 1994, which is a continuation of Ser. No. 17,958, Feb. 12, 1993, abandoned, which is a continuation of Ser. No. 709,900, Jun. 4, 1991, abandoned, which is a division of Ser. No. 488,490, Mar. 2, 1990, Pat. No. 5,063,204, which is a continuation of Ser. No. 64,846, Jun. 19, 1987, abandoned.

[30] Foreign Application Priority Data

Jan. 30, 1987 [DK] Denmark ................................. 499/87

[51] Int. Cl.⁶ .......................... A61K 38/08; A61K 38/22; A61K 38/24; A61K 38/27
[52] U.S. Cl. ................................... 514/12; 514/21; 514/8
[58] Field of Search ........................................ 514/12, 21

[56] References Cited

U.S. PATENT DOCUMENTS

| | | | |
|---|---|---|---|
| 4,973,577 | 11/1990 | Vale, Jr. et al. ............................ | 514/12 |
| 5,063,204 | 11/1991 | Jacobs ........................................ | 514/8 |

OTHER PUBLICATIONS

Steelman, S. L. et al. Assay of the Follicle Stimulation Hormone . . . Endocrinology Jul.–Dec. 1953 pp. 604–616.
Marshall, J. C. NEJM vol. 315(23) Dec. 4, 1986, pp. 1459–1468.
Goodman and Gilman, "The Pharmaceutical Bases . . . ", 3rd Ed, Macmillan Co. N. Y. 1965. pp. 1532–1533.
Bronson, I. H. Endocrinology vol. 118(6) 1986 pp. 2483–2487.
Leyendecker, G. J. Reprod Fert (1983) vol. 69 pp. 379–409.
Jacobs, Howard "Evidence for the Utility of Growth Hormone . . . The Somatotrophic Axis and the Reproductive Process in Health and Disease"1995 Springer–Verlag–NY pp. 279–290.
Advis, et al. Endocrinology vol. 108(4) 1981 pp. 1343–1352.
Laron, Z. Eur. J. Pediatr. 134.79–83 (1980).
Sheikolislam, B. M. Pediatrics, vol. 49(3) Mar. 1972 pp. 362–374.
Hammond, J. M. Aust J. Biol. Sci. vol. 34, pp. 491–504 (1981).
Hull, British Medical Journal vol. 291 Dec. 14, 1985, pp. 1693–1697.
Adashi, E. Y. et al. Endocrine Reviews vol. 6, No. 3 1985 pp. 400–420.
Jia, et al. Endocrinology vol. 118 No. 4 pp. 1401–1409 1986.
Hsuand Hammond, Endocrinology vol. 121 No. 4 pp. 1343–1348, p. 50, 1987.
Hsu+Hammond Growth Hormone Stimulates Insulin . . . Abstract 2, Presented At the Annual Meeting of the Society of Reproduction Cornell University, Ithaca, NY Jul. 14 17, 1986.
Hsu + Hammon Gonadotrophins and Estradiol, Abstract 762, Annual Meeting of Endocrine Society, Cal. Jun. 25–27 1986.
Hardin et al. Hormonal Regulation of Abstract 761 Annual Cal. Meeting of Endoctrine Soc. Jun. 25, 26, 27, 1986.
Aten. et al. GnRH—Like Ovarian Hormone . . . , Annual Meeting of Endocrine Society Cal. Jun. 25–27, 1986.
Hsu & Hammond, Endocrinology vol. 120, No. 1 1987 pp. 198–207.
Wilson, et al. J. Endocrinology vol. 104, pp. 179–183, 1985.
Combarnous, Y. et al. Annales d'Endocrinologie (Paris) vol. 45, pp. 261–268, 1984.
Matteri, et al. Domestic Animal Endocrinology vol. 3(1):39–48, 1986.
Davoren, J. B. et al. Endocrinology vol. 118 No. 2, pp. 888–890, 1986.
Goodman & Gilman's—The Pharmacological Basis of Therapeutics—6th Ed. 1980 p. 1376,
Scott, C. D. et al. Endocrinology vol. 116, No. 3 pp. 1102–1107, 1985.
VanWyk, J. J. et al. Relation Between Growth Hormone & Somatomedin Annu. Rev. Med. 1975, pp. 427–441.
Davoren, J. B. et al. Somatomedin Caugments . . . 1985 pp. E26–E33.
Adashi, et al. Endocrinology vol. 118 pp. 456–458 1986.
Adashi et al. Endocrinology vol. 117, No. 6 pp. 2313–2320, 1985.
March, C. M. Journal of Reproductive Medicine vol. 38 No. 5 May 1993 pp. 335–345.
Blumenfeld et al. Ann. NY Acad Sci 1991, 626, pp. 250–265.
Burger, et al. Clinical Endocrinology 1991, 35, pp. 112–122.
Goodman & Gilman, The Pharmaceutical Basis of Therapeutics 3rd. Ed. The Macmillan Co. pp. 1532–1533, 1965.
Shao-Yan Ying Inhibin and Beta Type BBRC 136:969–975 1986.
Davoren and Hsueh, Growth Hormone Increase Endocrinology 116:885 (1986).
Hull, et al. British Medical Journal vol. 291 p. 1693 (1985).
Von R. Illhardt, Z. Med. Labor techn. 12 (1971) p. 303–306.
Parlow, A. I. A Rapid Bioassay Method . . . Fed. Proc., 1958, vol. 17, 402.

(List continued on next page.)

*Primary Examiner*—Howard E. Schain
*Assistant Examiner*—P. Lynn Touzau
*Attorney, Agent, or Firm*—Ladas & Parry

[57] ABSTRACT

A combination of gonadotrophins and growth hormone is useful for treating infertility in higher mammals and humans since the probability of pregnancy is enhanced. In the treatment, gonadotrophins and growth hormone are injected separately, or a combined preparation containing both of these active substances may be used.

25 Claims, No Drawings

OTHER PUBLICATIONS

Ying, Shao–Yao, Endocrine Reviews vol. 9, No. 2, pp. 267–293, 1988.

Adashi, E. Y. et al. Endocrinology vol. 122, No. 4 pp. 1583–1591, 1988.

Adashi, E. Y. et al. Endocrinology vol. 116, No. 6, pp. 2135–2142, 1985.

Davoran, J. B. Endocrinology vol. 119, No. 5 pp. 2155–2162, 1985.

Adashi, et al. Molecular and Cellular Endocrinology, vol. 55, pp. 7–14, 1988.

Franchimont, P. Human Growth Hormone and . . . North–Holland Publishing Amsterdam; 1975 pp. 99–11.

Homburg, R. et al. Clinical Endocrinology vol. 29, 1988 pp. 1–5.

Jacobs, H. S. Advances in the Managment of Anovolution Highlights on Endocrinology pp. 343–347 First European Congress of Endocrinology, Copenhagen Jun. 1987.

Poretsky, L. Endocrine Reviews vol. 8, No. 2 pp. 132–141, 1987.

Steelman, S. L. Assay of the Follicle Stimulation Hormone . . . vol. 53 Dec. 1953, pp. 604–616.

Thorlaclus–Ussing, Acta Endocrinologica (Copenh), 1988, 117:65–72.

Vale, et al. Nature vol. 321 Jun. 1986 pp. 776–779.

Tsonis, et al. Nature vol. 321 Jun. 1986 pp. 724–725.

Erfahrangen mit einer speziallapparator Z. Med. Labortechn: 12:303 (171)1 Illharot.

PROCESS FOR TREATING INFERTILITY AND AN AGENT FOR USE IN THE PROCESS

This is a continuation of copending application Ser. No. 0 8/299,958 filed on Sep. 1, 1994 which is a continuation of application Ser. No. 08/017,958 filed on Feb. 12, 1993 (now abandoned) which is a continuation of application Ser. No. 07/709,900 filed on Jun. 4, 1991 (now abandoned) which is a divisional of application Ser. No. 07/488,490 filed on Mar. 2, 1990 (now U.S. Pat. No. 5,063,204) which is a continuation of application Ser. No. 07/064,846 filed on Jun. 19, 1987 (now abandoned).

The present invention concerns a process for treating infertility in higher mammals or humans. The invention also concerns an agent for use in the process.

Higher mammals and humans of the female sex are born with a large number of oocytes. For women, the number of egg cells is about 200,000 in each ovary. After birth, many egg cells are lost before pubescence, and no new ones are formed.

The oocytes are surrounded by a ring of epithelial cells, so-called granulose cells. The egg cell with the surrounding granulosa cells is called the follicle.

The ovarian function of higher mammals and humans is regulated by pituitary sex hormones, called gonadotrophins. These include the follicle stimulating hormone (FSH) which causes follicle maturation, and the luteinizing hormone (LH) which causes ovulation.

At the beginning of each menstruation the ovaries are affected by the FSH hormone, so that a plurality of follicles grows, several layers of granulosa cells are being formed, and the follicle is also surrounded by cells formed from the surrounding tissue, the theca cells.

Gradually, one follicle takes the lead, and the others degenerate. Normally, maturation of this one follicle takes 10 to 12 days. Also the amount of theca cells increases during the follicle maturation. Oestrogens are formed from these cells, and therefore increasing secretion of oestrogens will be a result of and thus a measure of the follicle maturation.

Halfway in the menstrual cycle the mature follicle bursts under the action of the LH released from the hypophysis, and the egg is discharged, ovulation. The egg passes out to the abdominal cavity and is caught by one Fallopian tube, through which it is conveyed to the uterus.

The follicle which has discharged the egg is transformed to a new hormone producing organ, the corpus luteum. Corpus luteum develops fully during the following days and produces progesterone together with oestrogens. Since progesterone is produced only in the corpus luteum, detection of progesterone implies ovulation with formation of a corpus luteum.

Corups luteum has a limited life of about 12–14 days. Then, it very quickly ceases functioning, and the blood content of oestrogens and progesterone drops abruptly. This decline causes necrosis of the lining of the uterus, and menstruation usually occurs 13 or 14 days after the ovulation.

The production and release of FSH and LH by the hypophysis is controlled partly from hypothalamus (a part of the brain positioned just above the hypophysis) by release of gonadotrophin releasing hormone (GnRH) and partly via a feed-back mechanism conditional upon the oestrogen production in the ovaries.

Release and activity of GnRH is modified by a so-called negative feed-back mechanism, since increased oestrogen production and thus increased oestrogen concentration in the blood take place in step with the follicle maturation. The increased oestrogen concentration impairs (i.e. has a negative effect on) secretion of FSH and LH from the hypophysis. Correspondingly, low oestrogen concentrations do not impair the GnRH secretion, and the release of GnRH from hypothalamus stimulates the release of FSH and LH from the hypophysis.

The causes of infertility in women include:

1) Abnormal ovarian function (primary ovarian failure)
2) Reduced hypothalamus-hypophysis function, i.e. hypophysis insufficiency, causing ovulatory failure (secondary ovarian failure)
3) Tubal damage (adhesions, obstruction, etc.)
4) Endometriosis (the presence of membranous material of the kind lining the uterus at other sites within the cavity of the pelvis).

Injections of gonadotrophins are used to treat infertility caused by hypophysis insufficiency. Usually, in the case of absent ovulation, first, daily injections are administered with preparations having FSH activity, such as menotrophin, until a pre-ovulation oestrogen content in urine or plasma can be detected. Then, one or two injections of chorionic gonadotrophin are administered, which cause ovulation and the formation and function of a corpus luteum.

The use of gonadotrophin preparations is not a certain method of treating infertility because a percentage of the treated women does not become pregnant. Further, the treatments involve a considerable risk, because overstimulation easily occurs, which may cause big ovarian cysts, liquid or blood accumulations in the abdominal cavity and liquid accumulation in the thoracic cavity. Further, there is a risk of multiple pregnancy (twins, triplets, quadruplets, etc.).

It is known that insulin and several of the growth factors can modify Some of the actions of gonadotrophins and granulosa cells (1). In these studies, granulosa cells from rats and pigs were cultured with FSH in serum free media in the presence of insulin, insulin-like growth factor 1 (IGF-1), transforming growth factor-beta (TGF-beta) and epidermal growth factor (EGF). These experiments showed that insulin and IGF-1 enhanced and EGF inhibited these actions of FSH. TGF-beta has been found to increase granulose cell aromatase activity (2).

In another series of experiments (3) it was shown that treatment of rats with growth hormone enhanced ovarian production of IGF-1.

The present invention is based on the surprising finding that growth hormones have a synergistic effect on gonadotrophins to stimulate ovarian function.

The process of the invention is thus characterized by treating the infertile individual with injections of a combination of gonadotrophins and growth hormone.

Owing to the synergistic effect it is possible to obtain a more certain result, i.e. the number of infertile women who become pregnant after a treatment is increased in per cent. Further, the necessary dose of gonadotrophins is reduced considerably, so that the danger of overdose is highly reduced.

The treatment may be performed on infertile farm animals, such as cows, pigs, sheep and minks. Further, infertile women can be treated with the present process so that ovarian function is normalized, and the chance of pregnancy is improved considerably.

According to the invention, the treatment may be performed with separate injections of gonadotrophins and growth hormone, respectively, over certain intervals of time. The normal treatment with gonadotrophins consists in daily injections with a gonadotrophin preparation. When this injection is supplemented every other day with growth hormone, ovarian response is improved considerably.

Instead, in a preferred embodiment of the process of the invention, a mixed preparation of gonadotrophins and growth hormone may be used, the dose size of the single components being adjusted individually. The amount of gonadotrophins is kept at a lower level so that overdosing is avoided, while providing an optimum effect.

To carry out the invention, use is made of an agent or an injection preparation which may expediently contain gonadotrophins and growth hormone in optimum or individually adapted amounts, distributed in a physiologically acceptable carrier of a type known per se in connection with injection preparations.

The growth hormone used should be the growth hormone specific to the species in question. Accordingly, human growth hormone, hGH, which may be biosynthetically produced, is used for women, and bovine GH for cattle, etc.

Infertility among couples is estimated to have an annual incidence of 1.2 couples for every 1,000 of the population (ref. 4). Of these couples around 20% have infertility problems due to abnormal gonadotrophin secretion causing avulatory failure (hypogonadotrophic hypogonadism, secondary ovarian failure).

"The indication for the combined treatment with gonadotrophin and hGH is hypogonadotrophic hypogonadism resistant to treatment with synthetic drugs stimulating ovulation (such as 'clomiphene') and where high doses of gonadogrophins are needed to develop mature follicles and eggs".

In patients with normal gonadotrophin secretion but abnormal ovaries (primary ovarian failure) the combined treatment with gonadotrophin and hGH is not expected to induce ovulation. Therefore, primary ovarian failure is not an indication for this kind of treatment.

Treatment with gonadotrophin and hGH can be used for "in vivo fertilization" where the objective is to obtain maturation of a single follicle and egg (oocyte) with the subsequent fertilization of this egg typically taking place the natural way, i.e. in the Fallopian tube. The above treatment can also be used for "in vitro fertilization", where the objective is to obtain as many mature follicles and eggs as possible. Next, the best looking eggs are removed (aspirated) from the patient's ovaries, and the subsequent fertilization of the eggs takes place in the laboratory. Hereafter a fertilized egg is placed in the uterine mucose of the patient, where the development of the egg continues.

The effect of treatment with gonadotrophin and hGH is hypogonadotrophic hypogonadism is illustrated below by means of 4 examples. The preparations used in all 4 cases were:

- Human Menopausal Gonadotrophin (HMG) containing menotrophin corresponding to 75 IU of FSH and 75 IU of LH per ampoule.
- Human Chorionic Gonadotrophin (HCG) containing 5000 IU of chorionic gonadotrophin per ampoule.
- Biosynthetic Human Growth Hormone (B-hGH) containing 20 IU of hGH per vial.

EXAMPLE 1

In vivo fertilization
Name: JN
Age: 35

Previous medical history: menarche (first bleedings) at the age of 15. Regular menstrual cycles for two years, but secondary amenorrhea (absence of the menstrual bleedings) since the age of 17. Failed to respond to clomiphene and therefore had HMG and HCG treatment for 12 cycles after which she conceived and delivered five years ago. For the last two years she has had HMG treatment with up to 80 ampoules of HMG per cycle, with no response (very low oestrogen levels and no follicular development).

First treatment cycle: (without B-hGH)

Daily injections of increasing doses of HMG for 35 days (totally 60 ampoules) followed by injection of 10,000 IU of HCG to induce ovulation. No satisfactory follicular development.

Second treatment cycle: (with B-hGH)

Daily injections of increasing doses of HMG for 21 days (totally 28 ampoules) followed by injection of 10,000 IU of HCG. During the same period the patient received injections of B-hGH: 20 IU administered three times per week (totally 180 IU of B-hGH). Eight well-defined follicles were performed.

Third treatment cycle: (with B-hGH)

Treatment regimen as above. Totally 23 ampoules of HMG injected during 18 days followed by 10,000 IU of HCG. B-hGH: 160 IU totally. Formation of 9 well-defined follicles.

EXAMPLE 2

In vivo fertilization
Name: PR
Age: 39

Previous medical history: primary amenorrhoea. No response to clomiphene. No response to LHRH (Luteinizing hormonere-leasing hormone). Had HMG and HCG treatment for about a year and needed 70–75 ampoules of HMG per cycle.

First treatment cycle: (without B-hGH)

During 29 days injection of totally 70 ampoules of HMG (followed by 10,000 IU and HCG) to incude formation of follicles.

Second treatment cycle: (with B-hGH)
Duration of treatment: 19 days
HMG: 35 ampoules
HCG: 10,000IU
B-hGH: 120 IU
Result: formation of 6 follicles.

Third treatment cycle: (with B-hGH)
Duration of treatment: 12 days
HMG: 29 ampoules
HCG: 10,000 IU
B-hGH: 100 IU
Result: formation of 8 follicles.

EXAMPLE 3

In vitro fertilization
Name: LLC
Age: 39

Previous medical history: menarche at the age of 11. Irregular cycles. 20 yeas ago—spontaneous pregnancy and delivery. In the last few years she has had clomiphene, gonadotrophins alone and with LHRH preparations and several in vitro fertilization attempts. There were difficulties in getting good eggs from this patient and this patient needed up to 160 ampoules of HMG to get a maximum of 2 eggs.

March 1987 treated with 33 ampoules of HMG for 11 days and 100 IU of B-hGH. Formation of 10 eggs, 3 of which were fertilized.

EXAMPLE 4

In vitro fertilization
Name: SH
Age: 38

Previous medical history: in 1982 ectopic pregnancy (development of a fetus at a site other than in the uterus) resulting in operation of the right Fallopian tube (salpingectomy). In 1983 surgery on the left Fallopian tube. Two years later—diagnose: massive pelvic adhesions. For the last two years treatment with clomiphene and HMG and several in vitro fertilization attempts.

November 1986 treated with 20 ampoules of HMG and buserelin (=gonadotrophin releasing hormone) as well as B-hGH resulting in the formation of 3 eggs, 2 of which were fertilized. One of the fertilized eggs was succesfully implanted in the uterus so that the patient becase pregnant. Synergistic Effect of Biosynthetic Human Growth Hormone (Norditropin$^R$ ) and Gonadotrophin in the Rat

Methods

Experimental animals

Female Sprague Dawley rats of the strain Crl:CD$^R$(S-D)BR were purchased at the age of 17–19 days, 30–33 g b. wt. From Charles River Wiga GmbH, Sandhoferweg 7, D-8741 Sulzfeld 1, BRD.

The rats were acclimatized for four days before use at 22°±2° C., 55±10% relative humidity, air change ten times an hour and light on from 6.30 to 18.30 h. During the acclimatization period the rats were housed with their mothers in rectangular Orth plastic cages, 27×35×16 cm with pine bedding type Hahnflock H ¾ from Hahn & Co. Kronsburg, D-2371Bredenbek, BRD. The animals had free access to Altromin diet 1324 (from Chr. Petersen A/S, DK-4100 Ringsted) and drinking water.

From sets of six litter mates, one litter mate from each set was randomnly allotted to each of six groups and marked according to litter. Six groups of eight rats were formed per experiment.

Hypophysectomy

Hypophysectomy was performed after the acclimatization period, when the rats were 21–23 days old. The rats were anaesthetized with amylenhydrate (10% in 0.9 saline), 4–5 ml/kg b. wt. in addition to 4–5 ml/kg Brietal$^R$ (10 mg/ml 0.9% saline) intraperitoneally. For the hypophysectomy use was made of a special apparatus described by R. Illhardt (5). After cutting the lower part of the ear the rats were fixated in the apparatus for transauricular hypophysectomy. A cannula was inserted into the hypophyseal area and the hypophysis was sucked out with a vacuum of 200–400 mm Hg. A cotton wool tampon was placed in the ear after the operation, and postoperatively the rats were treated with two daily injections (for two days) of Temgesic$^R$ for analgesia.

The rats were weighed before hypophysectomy and 14 days after (before use in the experiment), and only animals with a weight gain <10 g and a weight loss <4 g and in good health were used in the experiment.

Dosing

Groups of 8 hypophysectomized rats were given doses of Pergonal (Serono Menotrophine), 0.5 IU 1.0 IU and 1.5 IU, besides biosynthetic human growth hormone (Norditropin$^R$) or buffer (Nanormon$^R$) containing 20 g glycne, 2.5 g sodiumhydrogencarbonate, 2.0 g mannitol, and water for injections, to make 1000 ml. This buffer was used as a placebo. The three doses of Pergonal, which were chosen from the steep part of the dose response curve for Pergonal, were dissolved in 0.5 ml volumes of albumin — phosphate buffer pH 7.2 containing 14 IU of Chorionic Gonadotrophin (28 IU/ml). The doses were administered by subcutaneous injection three times with 24 hour intervals.

In one experiment 0.4 mg Norditropin$^R$ was administered in 0.5 ml volumes subcutaneously for three days to the groups given the three Pergonal doses, and 0.5 ml Nanormon$^R$ buffer was administered to three groups injected with the same three Pergonal doses. In a second experiment the same dose regimen was followed, only the Norditropin$^R$ dose was 0.6 mg in 0.5 ml.

About 24 hours after the last injection, the rats were killed by cervical dislocation and the ovaries removed and weighed immediately. The combined weight of both ovaries was recorded and used as test result for the individual rat.

Results

The data obtained are shown in tables 1–2. The tables show the ovary weights for the various dose groups, means ± S.E.M. The results for the Norditropin$^R$ injected groups were compared to the similar Nanormon$^R$ buffer injected groups using a student's t-test. The rats injected with Pergonal + Norditropin$^R$ had significantly higher ovary weights than the rats injected with Pergonal + buffer. Norditropin$^R$ shifted the dose response curve For Pergonal to the left. A maximal effect on the ovary weight seems to be reached by the combination of 1.0–1.5 IU Pergonal + 0.6 mg Norditropin$^R$ (table 2).

TABLE 1

| | Weight of ovaries from hypophysectomized rats injected with Pergonal and Norditropin ® or Nanormon ® buffer | | | | | |
|---|---|---|---|---|---|---|
| Doses | 0.5 IU | 1.0 IU | 1.5 IU | 0.5 IU | 1.0 IU | 1.5 IU |
| administered for three days | Pergonal + buffer | Pergonal + buffer | Pergonal + buffer | Pergonal + 0.4 mg Norditropin ® | Pergonal + 0.4 mg Norditropin ® | Pergonal + 0.4 mg Norditropin ® |
| Weight of ovaries (g), X̄ ± S.E.M. | 0.017 ± 0.001 N = 8 | 0.027 ± 0.002 N = 8 | 0.029 ± 0.004 N = 5 | 0.022* ± 0.002 N = 8 | 0.033* ± 0.002 N = 8 | 0.038* ± 0.002 N = 8 |

*$p < 0.05$ (student's t-test)

TABLE 2

| Doses | 0.5 IU | 1.0 IU | 1.5 IU | 0.5 IU | 1.0 IU | 1.5 IU |
|---|---|---|---|---|---|---|
| administered for three days | Pergonal + buffer | Pergonal + buffer | Pergonal + buffer | Pergonal + 0.6 mg Nordi- tropin ® | Pergonal + 0.6 mg Nordi- tropin ® | Pergonal + 0.6 mg Nordi- tropin ® |
| Weight of ovaries (g), X̄ ± S.E.M. | 0.019 ± 0.003 N = 6 | 0.024 ± 0.002 N = 7 | 0.033 ± 0.004 N = 6 | 0.024 ± 0.002 N = 7 | 0.044*** ± 0.003 N = 8 | 0.044 ± 0.004 N = 7 |

***$p < 0.001$ (student's t-test)

References

1. Adashi et al
   Insulin-like growth factors as intra-ovarian regulators of granulosa cell growth and function
   Endocrine Reviews 6: 400–420 (1985)
2. Ying et al
   Inhibin and beta-type transforming growth factor have opposite effects on the follicle stimulating hormone induced aromatase activity of cultured rat granulosa cells
   Bioch Biophys Res Commun 136: 969–975 (1986)
3. Benjamin Davoren and Hsueh A J W
   Growth hormone increases ovarian levels of immunoreactive somatomedin-C/insulin-like growth factor-I in vivo
   Endocrinology 118: 888–890 (1986)
4. Hull M G R et al Population study of causes, treatment, and outcome of infertility
   British Med J 291: 1693–1697 (1985)
5. Illhardt, R., 1971
   Erfahrungen mit einer Spezialapparatur zur transaurikularen Hypophysektomie bei Ratten.
   Z. med. Labortechn. 12: 303–306.

I claim:

1. A composition for treating infertility in mature higher female mammals, the composition comprising a combination of gonadotrophins and growth hormone present in indiviudally adapted amounts effective to enhance ovarian follicle and oocyte maturation in said mammal.

2. A composition according to claim 1 wherein the combination comprises a separate preparation of growth hormone and gonadotrophins each in a physiologically acceptable liquid carrier.

3. A composition according to claim 1 wherein the combination comprises a mixture of growth hormone and gonadotrophins in a physiologically acceptable liquid carrier.

4. A composition according to claim 1 wherein the growth hormone is species specific with regard to said mammal.

5. A composition according to claim 1 wherein the gonadotrophins are species specific with regard to said mammal.

6. A composition according to claim 1 wherein the growth hormone is human growth hormone.

7. A composition according to claim 1 wherein the gonadotrophins are human.

8. A composition according to claim 1 wherein the growth hormone is produced biosynthetically.

9. A composition according to claim 1 wherein the gonadotrophins are a combination of FSH and LH.

10. A composition according to claim 1 wherein the gonadotrophins are a combination of FSH, LH and hCG.

11. A composition according to claim 1 wherein the amount of growth hormone is adapted to be administered approximately every second day in a treatment cycle.

12. A composition according to claim 1 wherein the amount of gonadotrophins is adapted to be administered daily in a treatment cycle.

13. A composition according to claim 1 wherein the amounts of gonadotrophins is adapted to be administered in increasing amounts during a treatment cycle.

14. A composition according to claim 1 wherein the amount of growth hormone is adapted to be administered one time on a single day of a treatment cycle in a dose which is 20 IU.

15. A composition according to claim 1 wherein the amount of growth hormone to be administered in a treatment cycle is at least 100 IU.

16. A composition according to claim 1 wherein the amount of growth hormone to be administered in a treatment cycle is in the range of from 100 to 180 IU.

17. A composition according to claim 1 wherein the amount of gonadotrophins to be administered one time on a single day of a treatment cycle is in a dose which is 150 IU said dose comprising 75 IU of FSH and 75 IU of LH.

18. A composition according to claim 1 wherein the gonadotrophins to be administered in a treatment cycle comprise FSH and LH in amounts of at least 3450 IU.

19. A composition according to claim 1 wherein the amount of gonadotrophins to be administered in a treatment cycle comprises from 1725 IU FSH to 2625 IU FSH, from 1725 IU LH to 2625 IU LH, and from 0 IU to 10,000 IU hCG.

20. A composition according to claim 1 wherein the growth hormone and gonadotrophins are adapted to be administered in a treatment cycle which is in the range of from about 11 to 21 days.

21. A composition according to claim 1 wherein the gonadotrophins to be administered in a treatment cycle comprise FSH and LH in equal amounts, said amount being 10–25 times the amount of growth hormone to be administered in said treatment cycle.

22. A composition according to claim 1 wherein the gonadotrophins to be administered in a treatment cycle comprise FSH and LH in equal amounts the total amount of FSH and LH administered being from 20–50 times the amount of growth hormone to be administered in said treatment cycle.

23. A kit comprising growth hormone and gonadotrophins in separate preparations in individually adapted amounts effective to develop ovarian follicles and oocytes which are capable of being fertilized.

24. A kit comprising growth hormone and gonadotrophins in a mixture of individually adapted amounts effective to develop ovarian follicles and oocytes which are capable of being fertilized.

25. The composition according to claim 1 wherein the composition is administered by injection.

* * * * *